United States Patent [19]

Trammell

[11] Patent Number: 5,029,579
[45] Date of Patent: Jul. 9, 1991

[54] HYPERBARIC OXYGENATION APPARATUS AND METHODS

[75] Inventor: Wallace E. Trammell, Provo, Utah

[73] Assignee: Ballard Medical Products, Midvale, Utah

[21] Appl. No.: 392,169

[22] Filed: Aug. 10, 1989

Related U.S. Application Data

[63] Continuation of Ser. No. 297,351, Jan. 13, 1989, abandoned, which is a continuation of Ser. No. 61,924, Jun. 15, 1987, abandoned, which is a continuation-in-part of Ser. No. 865,762, May 22, 1986, abandoned.

[51] Int. Cl.$^5$ ............................................. A61H 9/00
[52] U.S. Cl. ................................. 128/205.26; 128/30; 128/202.12; 128/205.24; 604/23
[58] Field of Search ...................... 128/202.12, 205.26, 128/28, 30, 30.2, 38, 40, 402; 600/21; 604/23, 289, 290, 293, 304, 305, 308

[56] References Cited

U.S. PATENT DOCUMENTS

| | | | |
|---|---|---|---|
| 2,168,611 | 8/1939 | Thompson | 128/299 |
| 2,385,683 | 8/1945 | Burton | 128/298 |
| 2,531,074 | 11/1950 | Miller | 128/64 X |
| 2,896,612 | 7/1959 | Bates et al. | 128/60 |
| 3,269,388 | 8/1966 | Glascock et al. | 128/30 |
| 3,450,450 | 6/1969 | Hopkins et al. | 312/1 |
| 3,478,738 | 11/1969 | Altman et al. | 128/66 |
| 3,602,221 | 8/1971 | Bleicken | 128/204 |
| 3,712,298 | 1/1973 | Snowdon et al. | 128/40 |
| 3,744,491 | 7/1973 | Fischer | 128/184 |
| 3,749,091 | 7/1973 | Basa | 128/260 |
| 3,768,467 | 10/1973 | Jennings | 128/145 R |
| 3,786,809 | 1/1974 | Kitrilakis | 128/191 |
| 4,003,371 | 1/1977 | Fischer | 128/184 |
| 4,224,941 | 9/1980 | Stivala | 128/207.26 |
| 4,236,513 | 12/1980 | LoPiano | 128/184 |
| 4,296,743 | 10/1981 | Lasley | 128/30 |
| 4,328,799 | 5/1982 | LoPiano | 128/207.26 |
| 4,432,354 | 2/1984 | Lasley | 128/40 X |
| 4,448,189 | 5/1984 | Lasley | 128/25 R |
| 4,452,242 | 6/1984 | Bänziger | 128/205.26 |
| 4,467,798 | 8/1984 | Saxon et al. | 128/205.26 |
| 4,474,571 | 10/1984 | Lasley | 604/23 |
| 4,509,513 | 4/1985 | Lasley | 128/202.12 |
| 4,624,656 | 11/1986 | Clark et al. | 604/23 |
| 4,691,695 | 9/1987 | Birk et al. | 128/38 |

FOREIGN PATENT DOCUMENTS

| | | | |
|---|---|---|---|
| 317900 | 12/1919 | Fed. Rep. of Germany | 128/256 |
| 114443 | 12/1941 | United Kingdom | 128/248 |

OTHER PUBLICATIONS

TOPOX Literature.
Oxycure Literature.
B & F Medical Products, Inc. Literature.

Primary Examiner—Richard J. Apley
Assistant Examiner—Linda C. M. Dvorak
Attorney, Agent, or Firm—Lynn G. Foster

[57] ABSTRACT

A novel hyperbaric oxygenation apparatus, and related methods, the apparatus comprising a chamber in the form of a disposable inflatable bag of impervious inexpensive synthetic resinous material which can be used at any desired location, such as a hospital, a home or other site where oxygen can be appropriately made available. The pressure of the oxygen in the collapsible bag is pulsated between maximum and minimum positive values. The patient cyclically experiences first a medicinal increase in the blood gas levels in the limb under treatment with a corresponding restricted bloow flow and, thereafter, a progressive return to normal blood flow rates in the limb of the patient as the pressure in the chamber changes from maximum to minimum positive pressure. A respirator, normally used for intubated respiratory patients, in conjunction with a single oxygen influent/effluent port in hyperbaric oxygenation apparatus is efficacious to provide the oxygen and generate the desired pressure variations. Cuff inversion under positive pressure is prevented by anti-blowout structure.

5 Claims, 3 Drawing Sheets

HYPERBARIC OXYGENATION APPARATUS AND METHODS

This application is a continuation of U.S. patent application Ser. No. 297,351, filed Jan. 13, 1989, now abandoned which is a continuation of U.S. patent application Ser. No. 61,924, filed June 15, 1987, now abandoned which is a continuation in-part of U.S. patent application Ser. No. 865,762, filed May 22, 1986, now abandoned.

FIELD OF INVENTION

The present invention relates generally to oxygenation of a limb of a medical patient and more particularly to novel hyperbaric oxygenation apparatus, and related methods, by which a selected limb of a medical patient is effectively oxygenated.

PRIOR ART

While external hyperbaric oxygen chambers have been used over the years to treat the wounds, sores, etc. of medical patients, the following problems have persisted: (1) patient immobility, (2) lack of portability of the equipment, (3) failure to provide low cost hyperbaric equipment, (4) excessive cost for purchasing specially designed oxygen delivery equipment used in conjunction with hyperbaric chambers.

Patents known to the applicants are:

| | |
|---|---|
| U.S. Pat. No. 2,168,611 | U.S. Pat. No. 2,385,683 |
| U.S. Pat. No. 3,450,450 | U.S. Pat. No. 3,478,738 |
| U.S. Pat. No. 3,712,298 | U.S. Pat. No. 3,744,491 |
| U.S. Pat. No. 3,749,091 | U.S. Pat. No. 3,768,467 |
| U.S. Pat. No. 4,236,513 | U.S. Pat. No. 4,328,799 |
| U.S. Pat. No. 4,467,798 | U.S. Pat. No. 4,474,571 |
| U.S. Pat. No. 4,509,513 | West German 317,900 |
| British 114,443 | |

To the extent that the above-identified patents are relevant, they are individually and collectively of general interest only.

In the past, it has been advocated that expensive and complex equipment be fabricated for one specific purpose, i.e. to control the amount of oxygen delivered to and the pressure levels within a hyperbaric chamber. It has also been the common thinking within the medical field that the interior of hyperbaric chambers should be either maintained at a constant relatively high pressure or cycled between a maximum positive and a minimum vacuum pressure. The medical profession has retained a clear preference for massive, single location, expensive, iron lung-type hyperbaric chambers. In contrast the medical profession has been basically dissatisfied with previously proposed disposable hyperbaric chambers.

BRIEF SUMMARY AND OBJECTS OF THE INVENTION

In brief summary, the present invention overcomes or substantially alleviates the aforementioned prior art problems and provides a novel hyperbaric oxygenation apparatus, and related methods, the apparatus comprising a chamber in the form of a disposable inflatable bag of impervious inexpensive synthetic resinous material which can be used at any desired location, such as a hospital, a home or other site where oxygen can be appropriately made available. It has been found that by pulsating the pressure of the oxygen in the collapsible bag between maximum and minimum positive values, the patient cyclically experiences first a medicinal increase in the blood gas levels in the limb under treatment with a corresponding restricted blood flow and, thereafter, a progressive return to normal blood flow rates in the limb of the patient as the pressure in the chamber changes from maximum to minimum positive pressure. It has also been discovered that a respirator, normally used for intubated respiratory patients, can be efficaciously used preferably in conjunction with a single oxygen influent/effluent port in hyperbaric oxygenation apparatus embodying the principles of the present invention. Thus, influent oxygen is delivered to the bag encircling the limb of the patient until the bag is entirely inflated and the internal pressure thereof is at said maximum positive value. Influent delivery of oxygen is then temporarily terminated and effluent oxygen is thereafter slowly bled from the bag through the port at a controlled rate until the minimum positive pressure desired within the bag is reached and the bag is partially deflated. The cycle is then repeated.

The present hyperbaric oxygenation invention, therefore, provides for: use of an inexpensive efficacious existing source of oxygen, an inexpensive and reliable hyperbaric oxygenation apparatus and related methods, portability, disposability, improved patient mobility, economy, procedures which optimize the healing process and use of the apparatus at any one of several appropriate sites.

With the foregoing in mind, it is a primary object of the present invention to provide novel hyperbaric oxygenation apparatus and related methods.

A further important object of the present invention is to provide a novel hyperbaric oxygenation apparatus and related methods which overcome or substantially alleviate the aforementioned problems of the prior art.

It is an additional significant object of the present invention to provide a novel hyperbaric oxygenation apparatus comprising a chamber in the form of a disposable inflatable bag of impervious inexpensive synthetic resinous material.

It is a further dominant object of the present invention to provide a novel hyperbaric oxygenation apparatus wherein the pressure and delivery of oxygen into the hyperbaric chamber thereof is pulsated between maximum and minimum positive values causing the patient, at the limb under treatment to experience first a desirable increase in the blood gas levels in the limb under treatment notwithstanding a restriction on in blood flow and thereafter a return to normal blood flow in the limb.

A further object of paramount importance is the provision of the novel hyperbaric oxygenation apparatus and related methods wherein a respirator, normally used for intubated respiratory patients, is selectively used in conjunction with a hyperbaric oxygenation bag according the present invention by which oxygen is delivered through port means to the bag until the bag is entirely inflated and fully pressurized following which oxygen is slowly bled from the bag through the port means at a controlled rate until the minimum positive pressure is reached at which time the bag is partially deflated.

It is a further object of the present invention to provide a novel hyperbaric oxygenation apparatus and related methods having one or more of the following features: accommodates inexpensive efficacious use of an existing respirator, provides inexpensive and reliable hyperbaric oxygenation apparatus and related methods, provides for portability, disposability, improved patient mobility, economy, optimization in the healing process by control of the quantity and pressure of oxygen delivered to the apparatus and use of the apparatus at any of several appropriate sites.

These and other objects and features of the present invention will be apparent from the detailed description taken with reference to the accompanying drawings.

BRIEF DESCRIPTION OF THE DRAWINGS

FIG. 4 is a side elevation of the presently preferred oxygen port lounded upon the bag of the apparatus of FIG. 1;

DETAILED DESCRIPTION OF THE ILLUSTRATED EMBODIMENTS

Figure 1:
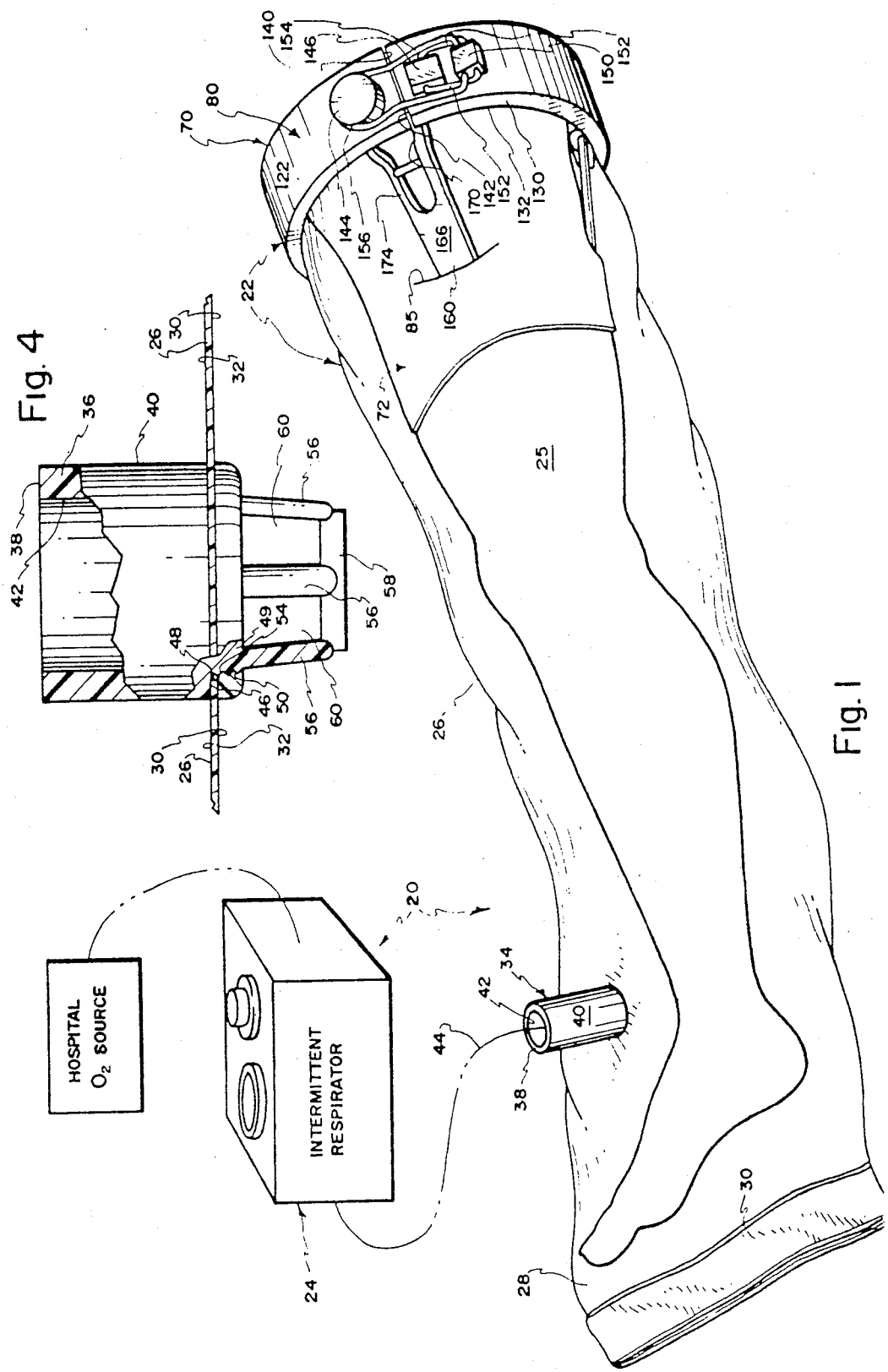
FIG. 1 is a perspective representation illustrating a presently preferred hyperbaric oxygenation apparatus according to the present invention installed upon a limb of a medical patient.

Reference is now made to the drawings wherein like numerals are used to designate like parts throughout. FIG. 1 illustrates, in perspective, a presently preferred hyperbaric oxygenation system, generally designated 20. System 20 comprises a hyperbaric oxygenation chamber apparatus, generally designated 22 and an intermittent respirator, generally designated 24, of the type generally used in respiratory for intubated patients. The apparatus 22 is illustrated as being operatively installed upon a leg 25 of a patient.

The hyperbaric apparatus 22 comprises a collapsible and inflatable bag 26 of gas impervious synthetic resinous film, such as by-axial polyvinyl chloride. The bag 26 is illustrated as being in the form of a length of cylindrical sleeve stock. The distal end 28 is closed and hermetically sealed. A heat seal seam 30 is presently preferred for purposes of closing and sealing the distal end 28 of the tubular bag 26. Utilization of heat sealing is an inexpensive, readily available technique which provides for reliable impervious closure of the distal end of the bag 26. The closure 30 also facilitates convenience in packaging and shipping the apparatus 22.

The bag 26 is preferably formed from single ply material and defines a hollow interior 32 (FIG. 3) sized to comfortably receive the limb 25 for oxygenation. The bag 26 is illustrated as having a wall thickness 32 whiCh is substantially uniform throughout.

Figure 5:
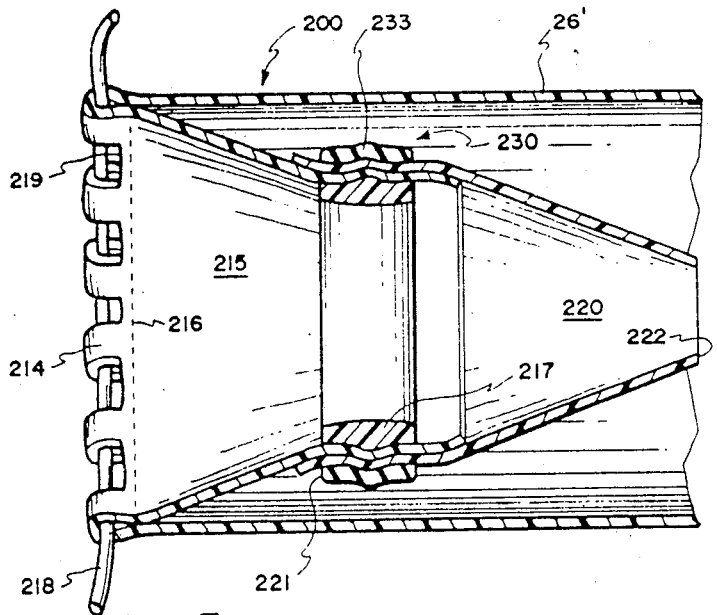
FIG. 5 is a fragmentary cross-section of the proximal end of the second presently preferred hyperbaric oxygenation apparatus according to the present invention.

The hyperbaric mechanism 22 comprises a single rigid oxygen port 34 (FIGS. 1 and 4) which accommodates both influent and effluent flow of oxygen into and from the hollow interior 30 of the bag 26. The port 34 comprises an annular outwardly projecting wall 36 which terminates in an elevated blunt edge 38. The annular wall 36 is illustrated as being of uniform thickness disposed external of the bag 26 and defined by an outside cylindrical surface 40 and an interior cylindrical surface 42 where a fluid communicating tube 44, diagrammatically illustrated in FIG. 1, is connected in a conventional manner. Preferably the material from which the oxygen port 34 is fabricated is a satisfactory synthetic resinous material in shape-retaining rigid form, such as medical grade injection molded polyurethane. The wall 36 is reduced in its outside diameter at surface 40 at shoulder 46, which shoulder contiguously engages the bag 26. The shoulder 46 is sized so as to correspond in size and be aligned with an aperture 48 formed in the bag 26. The shoulder 46 merges with a projection 49 comprising threads 50, disposed essentially within the hollow interior 30 of the bag 26 adjacent to the aperture 48. A ring 52 comprising a threaded aperture 54 is tightened upon the threads 50 and against the bag 26 to compressively hold the bag 26 adjacent to the aperture 48 between the shoulder 46 and the ring 52, as best illustrated in FIG. 5.

The projection 49 merges into a plurality of spaced inwardly extending arms 56, the respective distal ends of which are integrally secured to a flat baffle plate 58. Thus, air entering the bag 26 through the port 34 will pass along the bore 42, against the baffle plate 58 and into the hollow interior 30 of the bag 26 transversely of the port 34 through the openings 60 between the spaced arms 56. Accordingly, the air is prevented from directly striking the limb 25 of the patient.

The hyperbaric apparatus 22 also comprises a proximal end assembly, generally designated 70, by whIch the proximal end of the mechanism 22 is releasably hermetically sealed to the limb of the patient undergoing oxygenation treatment in such a way as to prevent inadvertent, undesired loss of positive pressure from the interior 38 of the bag 26, as hereinafter more fully explained.

The proximal end assembly 70 comprises an elastic tapered sleeve or cuff, generally designated 72, a ring 74 (FIG. 3), which iş secured to the proximal end of the bag 26 as hereinafter more fully explained, a collar, generally designated 76, a plurality of separate cuff-retaining struts, each generally designated 78, and a compression collar clamp, generally designated 80.

Figure 3:
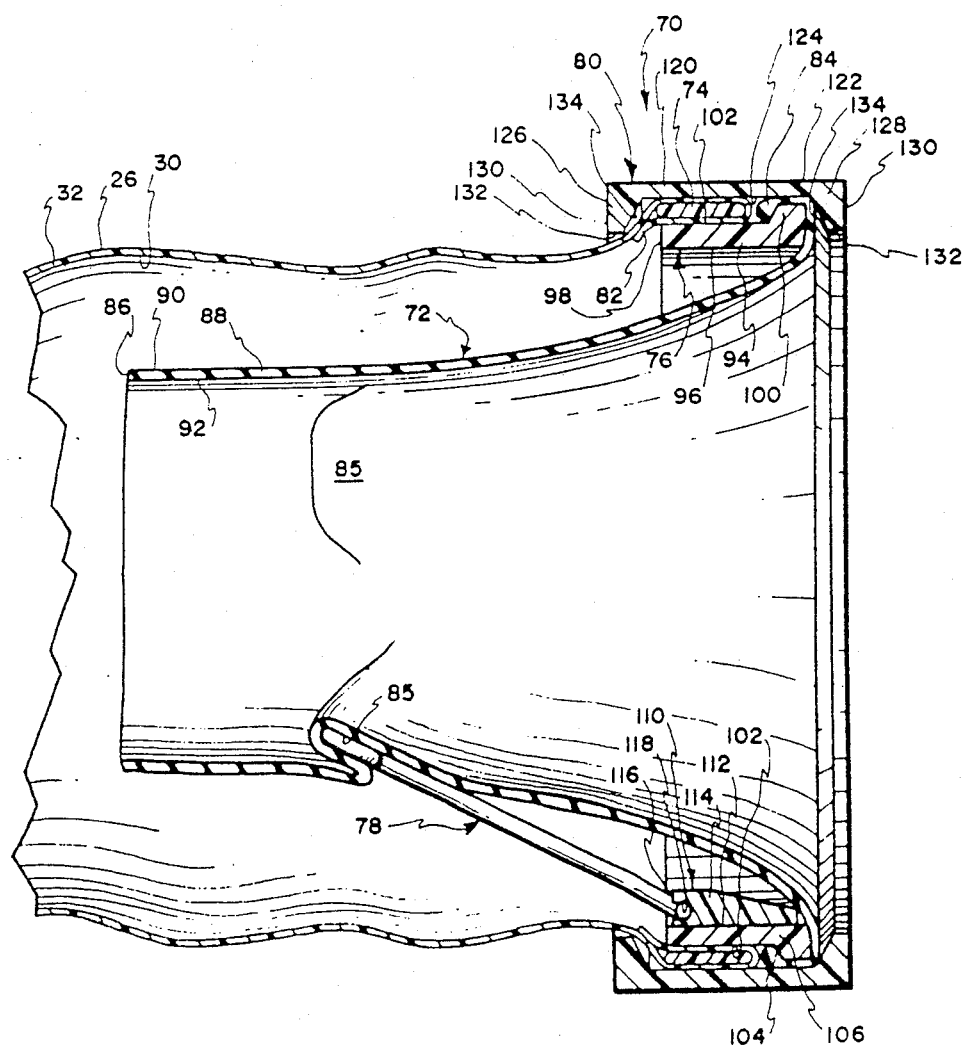
FIG. 3 is an enlarged fragmentary cross-sectional view of the assembled proximal end of the apparatus of FIG. 1.

The bag 26, illustrated as being a cylindrical sleeve, is secured to the ring 74 by interposing a suitable adhesive between the surfaces of the ring 74 and the bag wall 32 to be overlapped and wrapping the proximal end 82 of the bag around the ring 74, as best illustrated in FIG. 3. The wrapping is illustrated as being first over the top surface of the ring 74, then around the trailing edge of the ring 74 and thence along the bottom surface of the ring 74. Thus, the proximal end 82 of the bag wall 32 is in the form of an annular loop which encases the ring 74. The ring 74 is illustrated as being a flat band preferably rigid, formed from a suitable synthetic resinous material, such as polyurethane using conventional injection molding techniques.

The cuff or sleeve 72 is illustrated as being tapered convergently from an annular enlarged trailing end lip 84 thereof to the distal blunt edge 86 thereof. when in an unstressed state. Preferably, the sleeve or cuff 72 extends for a considerably greater distance than is illustrated in the Figures with a continuing convergent conical taper back to front. At the time of installation of the apparatus 22 upon the limb 25 of the patient, the diameter of the limb adjacent to the proximal end assembly 70 is sized and coordinated with the enlarging diametral dimension of the cuff 72. A cut line is made with a suitable instrument to form blunt edge 86.

The diametral dimension at edge 86 is selected to be slightly smaller than the diametral dimension of the limb 25 at the site where the cuff 72 is to be contiguously located. In that way, insertion of the limb through the cuff 72 will enlarge the previously unstressed diametral dimension of the cuff at and near the blunt edge 86 so that the sleeve 72 will exert a relatively wide compressive radial force upon the limb 25. The cuff 72 is illustrated as comprising a thin wall 88 having a uniform thickness throughout and comprising outside wall surface 90 and interior wall surface 92.

Intermediate the edge 86 and the lip 84 of the cuff 72 are three pockets 85 integrally formed in the cuff 72. Each pocket 85 is, therefore, integral with the wall 88 of the cuff 72 and has an internal longitudinal length and an internal width selected to accommodate receipt of the respective support struts 78 as hereinafter more fully explained. The pockets are illustrated as being disposed at 120 degree intervals around the sleeve 72.

The collar 76, of the proximal end assembly 70, is preferably formed of rigid synthetic resinous material, such as polyurethane, using conventional injection molding techniques. The collar 76 comprises a generally annular configuration comprising a wall 94. The wall 94 comprises an internal cylindrical surface 96 a blunt leading edge 98 and a chamfered trailing edge 100. The wall 96 also comprises an exterior cylindrical surface 102, which is longitudinally stepped at angular shoulder 104 to form an enlarged trailing annular lip 106. The diameter of the external surface 102 is slightly smaller than the diameter of the inside surface of the ring 74. Thus, the ring 74 with the proximal end 82 of the bag wall 32 wrapped therearound may be snugly force-fit over the surface of 102 in the manner best illustrated in FIG. 3.

The outside diameter of the trailing flange or lip 106 is substantially greater than the at rest diameter of the trailing lip 84 of the cuff or sleeve 72. The proximal end of the sleeve 72 is assembled into the position illustrated in FIG. 3 by diametrally manually stretching the diameter of the trailing lip 84 and the adjacent wall 82 of the cuff 72, while inverting the lip 84 upon the sleeve wall 88 and forcing the lip 84 over the annular lip 106 and against the surface 102, as shown in FIG. 3. In this position, the memory of the material from which the ring or enlarged lip 84 and the wall 88 of the cuff 72 is made will exert a compressive stress upon the collar 76 thereby holding the proximal end of the cuff 72 in the described stretched condition.

The collar 76 also comprises, as illustrated, three strut-retaining clips, each generally designated 110. Each clip 110 is secured to the inside surface 96 of the collar 76, at interface 112, using a suitable adhesive, bonding agent or the like. Each clip comprises a body of material 114 which comprises a forwardly exposed edge 116, in which is disposed a generally transverse keyhole shaped slot 118, for purposes yet to be explained.

Each strut 78 is preferably of one piece injection molded manufacture comprising a suitable synthetic resinous material, such as rigid polyurethane. Each strut 78 comprises a wide arcuate distal shoe or foot 160 which comprises a thin arcuate wall having a curvature substantially the same as the curvature of the cuff wall 88. The wall forming the arcuate shoe 160 is illustrated as being of uniform thickness and spans transversely between one rounded side edge 162 to a second rounded side edge 164. The distance transversely spanned by the shoe 160 between side edges 162 and 164 is substantially equal to the transverse width of the pocket 85 into which the foot 160 is placed in the assembled condition, as best illustrated in FIG. 3. Thus, the wide foot 160 is situated entirely within the associated pocket 85 and is there retained against inadvertent separation. Preferably this strut placement occurs after sleeve 72 is mounted upon collar 76 and before ring 74 is positioned upon collar 76.

Each strut 78 also comprises a load transmitting central essentially linear bar 166. The central bar 166 is integrally joined, at site 168, to the foot 160 and comprises a length selected to be substantially that distance between the opening to the associated pocket 85 and the base of the keyway slot 118 in the associated clip. The trailing end of the central bar 166 comprises an aperture 170, which is bridged at the proximal end by a transverse bridge 172. Bridge 172 is integral with parallel wall segments 174 and 176. The aperture 170 and the bar 172 are sized so that the keyhole shaped slot 118 of the associated clip 110 will accommodate an interference-fit acceptance of the bar 172 in the fully assembled condition, as illustrated in FIG. 3.

It has been found that by utilization of the struts 78 placed diagonally, as illustrated in FIG. 3, between the sleeve pockets 85 and the clips 110, longitudinal and inwardly directed radial forces are exerted upon the cuff 72 which prevent inversion or blowout of the cuff and thus prevent undesired pressure loss at the proximal end of the apparatus during use.

Once the assembled proximal bag end 82 and ring 74 are placed in the position illustrated in FIG. 3, the struts 78 are in place and the enlarged lip 84 of the cuff 72 is likewise placed in its stretched inverted posture over the radially enlarged flange 106, the collar clamp 80 is ready for placement at the proximal end 70.

The collar clamp 80 comprises an annular wall 120 which is split at one location and has a front-to-back dimension which is greater than the front-to back dimension of the collar 94. The wall 120 comprises an exposed external cylindrical surface 122 and an internal cylindrical surface 124, the longitudinal distance of which is slightly greater than the longitudinal dimension of the collar wall 94. The wall 120 is interposed between and integral with inwardly directed radially disposed front and back flanges 126 and 128. The flange 126 comprises a leading blunt edge surface 130, a cylindrical shoulder 132 and an annular diagonally directed surface 134. which merges with surface 124. The trailing flange 128 is similarly constructed and numbered, though of opposite hand.

The diameter of the inner surface 124 of the wall 120 is selected so that wall 120 is caused to exert radial pressure upon the proximal end 82 of the bag 26, the ring 74 and the trailing lip 84 and adjacent wall 88 of the cuff 72 to retain the assembled condition once the proximal end assembly 70 is fully assembled and clamped.

Figure 2:
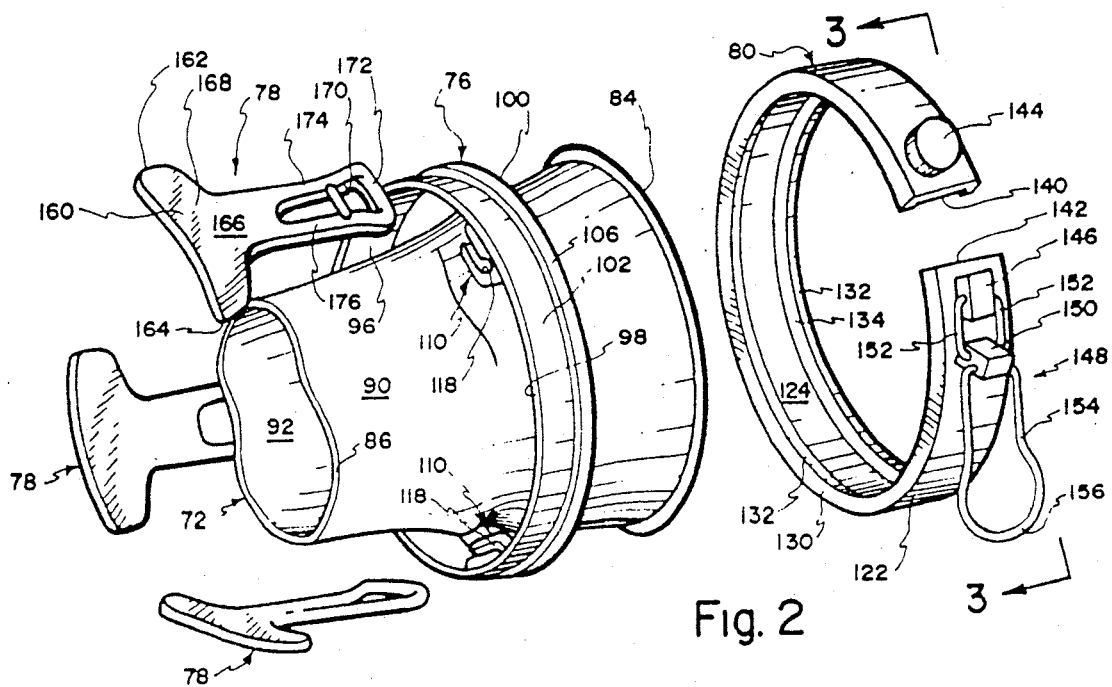
FIG. 2 is a fragmentary exploded perspective of the proximal end of the apparatus of FIG. 1.

The collar clamp 80 is axially slit to form ring edges 140 and 142. See FIG. 2. A male annular button 144 is integrally secured to the exterior surface 122 of the wall 120 adjacent the blunt slit edge 140, while a rectangular clamp mounting abutment block 146 is integrally secured to the external surface 122 of the wall 120 adjacent the slit edge 142. The block 146 carries a toggle clamp 148. The toggle clamp comprises a toggle block 150, which is secured by parallel embedded wires 152 to the mounting block 46. A latch wire 154 having an enlarged loop 156 is also anchored in the toggle block 150. Accordingly, the collar clamp 80 may be manually diametrically enlarged and axially superimposed upon the otherwise assembled portions of the proximal end assembly 70 until the collar clamp 80 is in accurate radial alignment therewith. The enlarged loop 156 is placed over the cylindrical button 144 and the toggle mechanism 148 manually closed into its locked condition, as best illustrated in FIG. 1. This will compressively radially hold the assembly 70 in its assembled relationship.

It has been discovered that by pulsating the pressure and delivery of oxygen to the bag 26 encapsulating the limb 25 between maximum and minimum positive values, which may be selectively set for any given patient depending upon the health and condition of the patient, the patient cyclically experiences first a desirable increase in the blood gas levels accompanied restricted blood flow within the limb of the patient under treatment and thereafter a return to normal blood flow rates within said limb. Surprisingly, it has been found that utilization of an existing hospital or like respirator normally for use with intubated respiratory patients, can be connected to the apparatus 22. Oxygen delivered from the respirator to the bag 26 cyclically first until the bag is entirely inflated and the internal pressure thereon is at a predetermined maximum positive value desirable for enhancement of blood gas levels in the patient and thereafter, with delivery of the oxygen temporarily terminated by the respirator, oxygen is slowly bled from the bag through the port 34 until the bag is partially deflated and the minimum desired positive oxygen pressure within the bag is obtained. Thereafter, the cycle is repeated.

While any suitable respirator with appropriate capacity can be used, it is presently preferred that the Bird Mark Seven be used. The Bird Mark Seven is a positive pressure, positive-cycled, assistor-controller (pneumatic) ventilator available from the Bird Corporation. The pressure settings available on the Bird Mark Seven range from 0 to 60 cm water pressure at 50 psi. Cycle times may be set as desired.

Reference is now made to FIG. 5, which illustrates another proximal end assembly, generally designated 200. Proximal end assembly 200 comprises the impervious hyperbaric oxygenation bag 26', identical to heretofore described bag 26, except as hereinafter indicated. Bag 26' is inwardly reversed upon itself and sealed or stitched to itself along line 216. Notches 219 are cut, as illustrated. Thus, a series of loops 214 through which a drawstring 218 is caused to pass are created.

The bag 26' inwardly beyond line 216 is gathered so as to present a truncated conical configuration at section 215. The distal end of the cone-shaped section 215 of the inwardly directed proximal end of the bag 26' in connected to the larger proximal end of a cone-shaped sleeve or cuff 220. As stated earlier the cuff 220 is formed of highly stretchable sealing material, such as latex rubber, designed to be sized for a particular use by cutting to form the blunt end 222 having a diametral size selected to snugly and sealingly fit the limb of the patient placed within the hyperbaric oxygenation bag 26', in the manner heretofore described.

The juncture between the small leading end 221 of the frustoconical end 215 of the bag 26' and the large end of the cuff 220 is made permanent by a rigid internal ring 217 sized so as to require the large end of the cuff 220 to be stretched over the end of the distal end of the frustoconical section 215 of the bag 26'. An elastic band 233 having an unstressed diameter less than the outside diameter of the band 217 is stretched and placed over the assembled proximal end of the cuff 220 to complete the compression joint 220.

When the hyperbaric oxygenation apparatus comprising hyperbaric oxygenation bag 26' is properly installed upon the limb of a patient for treatment, as heretofore described, the drawstring 218 is manually tied snugly and contiguously to the limb of the patient. Hence, the interior of the bag 26' may pulsatingly receive oxygen at predetermined intervals causing the positive pressure and oxygen level within the bag 26' to vary between predetermined maximum and minimum values thereby cyclically fully inflating the bag 26' at maximum positive pressure and partially deflating the bag 26' at minimum positive pressure.

Figure 6:
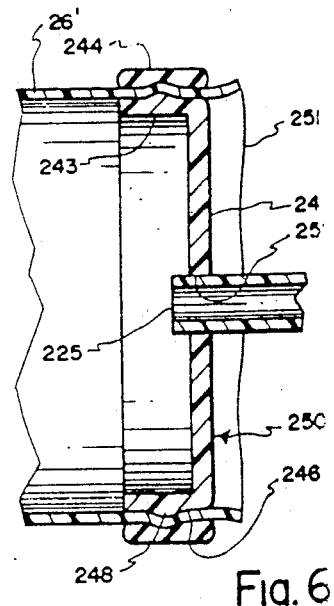
FIG. 6 is a fragmentary cross-section of the distal end of a second presently preferred hyperbaric oxygenation apparatus according to the present invention.

Reference is now made to FIG. 6, which illustrates a second embodiment for closing the distal end a hyperbaric oxygenation bag 26' in accordance with the principals of the present invention. Bag 26' is illustrated as terminating in an essentially blunt, cut edge 251. Disc-shaped closure 250 is inserted through the open end of the bag 26' at end 251. The outside diameter of the disc-shaped member 250 is illustrated as being substantially the same as the inside diameter of the tubular shaped bag 26'. More specifically, the disc-shaped member 250 comprises a flat circular-shaped end wall 242 which extends transverse of the axis of the bag 26'. Wall 242 merges with an axially directed annular flange 243. Flange 243 and bottom wall 242 are illustrated as being of uniform thickness and essentially form a plug in the distal end of the tube 26'. The external surface of flange 243 at 246 comprises an outwardly directed annular rib 248. The disc-shaped member 250 also comprises an oxygen inlet/outlet port 225 integrally joined to the wall 242 in the sealed relation at aperture 252. Thus, in the embodiment of FIG. 6, the bag 26', unlike bag 26 as heretofore described, would not have an oxygen port in the wall thereof. The interior of the bag 26', in terms of influent and effluent oxygen, is serviced by the single port 225.

If desired, the bag 26' may be bonded or glued to the exterior surface 246. As illustrated, an elastic band 244, having an unstressed diameter less than the diameter of the flange 243, is stretched over the bag end 251 and the disc-shaped member 250 in radial alignment therewith and carefully released so as to compressively hold the closure 250 in sealed relation with the distal end of the bag 26' as illustrated in FIG. 6.

Figure 7:
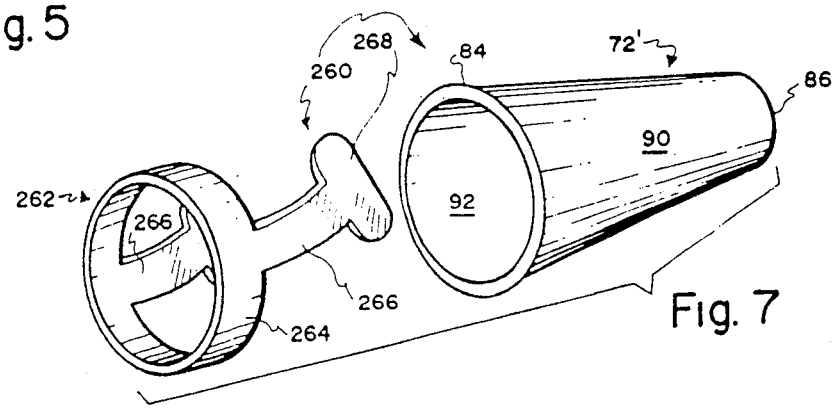
FIG. 7 is an exploded fragmentary perspective of a further sleeve-retainer and sleeve assembly forming part of the present invention.

Reference is now made to FIGS. 6 and 7 which illustrate an additional anti-blowout assembly, generally designated 260 according to the principles of the present invention. For ease of illustration, the bag and some of the proximal end assembly have been removed for purposes of clarity. It should also be understood that the anti blowout mechanism 260 is used at the proximal end of a hyperbaric oxygenation apparatus of the type heretofore described. The assembly 260 is illustrated as comprising a sleeve or cuff 72' identical to the cuff 72 heretofore described except the pockets 85 are removed. No further description of sleeve 72' is believed to be necessary.

Figure 8:
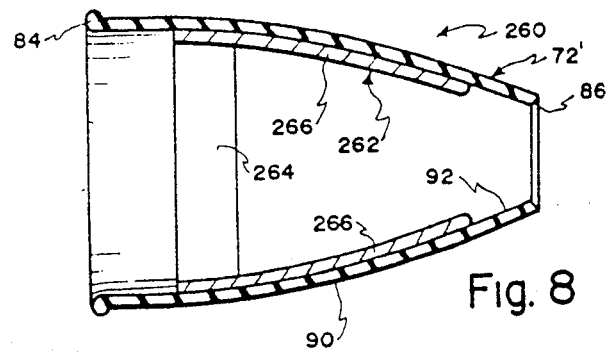
FIG. 8 is a fragmentary cross-sectional view of the assembled sleeve-retainer and sleeve embodiment of FIG. 7.

The assembly 260 also comprises the bracket, generally designated 262. The bracket 262 is preferably formed of rigid noncorrosive metal or plastic. The bracket 282 comprises an annular ring or band 264 of uniform thickness throughout defining uniform inside and outside diameters. The axial length of the ring 264 is relatively short. Integral with the ring at 264 are two opposed forwardly projecting inwardly converging struts or arms 266, which are illustrated as containing a slight curvature. Each arm 266 terminates in an enlarged foot 268. By placing the bracket 262 snugly within the interior of the sleeve 72' the ring 264 is sized so that it comes to rest within the proximal exterior of the sleeve 72' as illustrated in FIG. 8. Thus, when assembly 260 forms an integral part of the proximal end assembly of the present invention, as heretofore described, inversion of the sleeve 72' is prevented by the internal reinforcement supplied by the bracket 262, primarily at fingers 266.

Figure 9:
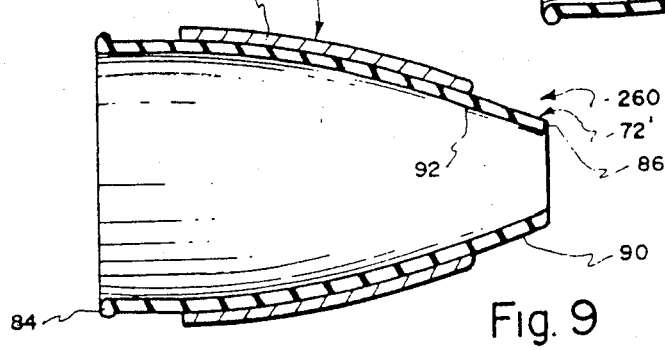
FIG. 9 is a fragmentary cross-sectional view similar to FIG. 8 illustrating the sleeve-retainer disposed outside of rather than inside of the sleeve.

In reference to FIG. 9, by correctly sizing the bracket 226 and the sleeve 72' the sleeve may be placed inside of the bracket 262 and secured thereto by adhesive or any other suitable connector to similarly prevent sleeve or cuff inversion or blowout.

The invention may be embodied in other specific forms without department from the spirit or essential characteristics thereof. The present embodiments, are, therefore, to be considered in all respects as illustrative and not restrictive, the scope of the invention being indicated by the appended claims rather than by the foregoing description, and all changes which come within the meaning and range of equivalence of the claims are therefore to be embraced therein.

What is claimed and desired to be secured by United States Letters Patent is:

1. A method of oxygenating a limb of a patient comprising the steps of:
   (a) encapsulating a selected limb of the patient having an exposed injury within an inflatable disposable impervious hollow collapsible bag which is closed at the distal end thereof, comprises a single site two way input/output means for communication with an existing intermittent patient respirator which is respiratorically idle, and means releasible sealed to the limb of the patient at the proximal end thereof;
   (b) releasibly placing the single site two way input/output means in fluid communication with the existing intermittent patient respirator which provides oxygen at a selectable positive pressure at selectably variable pressure cycling rates;
   (c) placing the intermittent patient respirator in communication with a source of oxygen under substantially constant positive pressure;
   (d) setting the patient respirator to a desired fluid pressure cycling rate and to a relatively high maximum pressure;
   (e) constantly delivering oxygen under said substantially constant positive pressure from said source to the respirator;
   (f) delivering a predetermined quantity of influent oxygen from the respirator through the single site two way input/output means to the hollow interior of the bag whereby the preselected relatively high positive pressure is periodically produced in the interior of the bag restricting blood flow in the encapsulated limb over a short span of time while maintaining the seal at said proximal end whereby the bag is inflated;
   (g) terminating delivery of said influent oxygen from the respirator to the interior of the bag for a second relatively short span of time while exhausting oxygen from the bag through the single site two way input/output means to the respirator and therefrom to the atmosphere to at least partially deflate the bag thereby decreasing the positive pressure within the bag from the relatively high positive value to a lower positive value which accommodates restoration of blood flow but still delivers oxygen under positive pressure to the wound, while maintaining the seal at said proximal end;
   (h) repeating steps (f) and (g) successively over a protracted period of time to cyclically oxygenate the limb between the relatively high and lower positive pressures.

2. A hyperbaric oxygenation apparatus comprising:
   a source of oxygen constantly available under substantially constant pressure;
   an existing intermittent patient respirator, which is usable but not being used for respiratory therapy connected to the source of oxygen comprising means periodically delivering oxygen to an output side of the respirator, at a preselected pressure and rate, and means by which earlier delivered oxygen is exhausted to the atmosphere;
   a portable hyperbaric chamber comprising an elongated disposable bag of gas impervious synthetic resinous film comprising a hollow interior in which a limb of the patient is disposed for oxygenation, means imperviously closing the distal end of the bag, single site input/output port means by which the oxygen is periodically delivered to and exhausted from the hollow interior of the bag, through direct single connection means to the respirator causing the bag to sequentially expansively inflate and contractively partially deflate, proximal end means sized to surround the limb of the patient, the proximal end means comprising means which are caused to compressively engage the limb of the patient so as to hermetically seal the proximal end of the bag against the limb of the patient.

3. A method of oxygenating a limb of a patient comprising the steps of:
   (a) encapsulating a selected limb of the patient having an exposed injury within an inflatable disposable impervious hollow collapsible bag which is closed at the distal end thereof and releasibly sealed to the limb of the patient at the proximal end thereof;
   (b) releasibly placing the hollow interior of the bag in fluid communication with a source of oxygen supplying oxygen at a substantially constant pressure to a patient respirator which is usable but not being used for patient respiratory therapy, but is currently not used and which intermittently supplies oxygen at a selectable positive pressure and exhausts oxygen earlier supplied to the atmosphere;
   (c) passing a predetermined quantity of influent oxygen from the source through the respirator to the hollow interior of the bag through a single site input/output port over a short, preselected span of time until the internal pressure within the bag reaches a predetermined relatively high selected positive value which restricts blood flow and the bag is inflated;

(d) terminating passing of said influent oxygen through the respirator to the interior of the bag and exhausting oxygen from the bag through the same single site input/output port and then through the respirator to the atmosphere for a second relatively short, preselected span of time thereby decreasing the positive pressure within the bag from a relatively high positive value to a lower positive value which accommodates the restoration of uncurtailed blood flow but nevertheless delivers oxygen under positive pressure to the wound thereby only partially deflating the bag;

(e) repeating steps (c) and (d) successively over a protracted period of time.

4. A pulsatile flow hyperbaric chamber system which uses an existing respiratorically idle patient respirator to provide pulsatile pressure at manually selectable variable rates and pressure levels, said system comprising:

a source of gas continuously available comprising oxygen used in the hyperbaric chamber;

the respirator comprising means by which respiratory modifications are selectively made to the gas influent comprising humidification, intermittent flow control for both delivery of the gas, maximum and minimum gas pressure level control, and pulsatile rate control;

a disposable, portable hyperbaric chamber comprising an elongated inflatable collapsible bag comprising a body of gas impervious synthetic resinous film comprising a hollow interior in which a limb of the patient is disposed for treatment, proximal end means, means imperviously closing the distal end of the bag, two way single site input/output means in communication with the respirator to receive and exhaust gases which intermittently provide higher and lower pressures within the bag, but continuously maintain at least partial bag inflation;

the chamber further comprising proximal end means sized to surround the limb of the patient, the proximal end means comprising means which are caused to compressively but manually releasibly engage the limb of the patient so as to maintain and hermetically seal the proximal end of the bag against the limb of the patient.

5. A disposable, portable hyperbaric chamber and patient attachment means adapted for use with an idle breathing therapy respirator, comprising means by which respiratory modifications are made to a gas influent comprising humidification, intermittent flow control for both deliver of the gas, maximum and minimum pressure level control and pulsatile rate control, said means comprising:

the disposable, portable hyperbaric chamber comprising an elongated collapsible inflatable bag comprising a body of gas impervious synthetic resinous film comprising a hollow interior of variable internal volume in which a limb of the patient is disposed for treatment, proximal end means, means imperiously closing the distal end of the bag, two way single site input/output mean sin communication with the respirator to receive and exhaust gases which intermittently provide higher and lower pressures within the bag, but continuously maintain at least partial bag inflation, thereby causing the internal volume of the bag to vary;

the chamber further comprising disposable proximal end means sized to surround the limb of the patient, the proximal end means comprising means which are caused to compressively but manually releasibly engage the limb of the patient so as to maintain and hermetically seal the proximal end of the bag against the limb of the patient.

* * * * *